United States Patent [19]

Jennings

[11] 4,327,573
[45] May 4, 1982

[54] METHOD AND APPARATUS FOR DETERMINING THE LOW TEMPERATURE CHARACTERISTICS OF MATERIALS

[75] Inventor: Thomas A. Jennings, Bala Cynwyd, Pa.

[73] Assignee: T. A. Jennings Associates, Inc., Bala Cynwyd, Pa.

[21] Appl. No.: 125,790

[22] Filed: Feb. 29, 1980

[51] Int. Cl.³ .................. G01N 25/04; G01N 27/14
[52] U.S. Cl. .................. 374/10; 324/65 R; 374/21
[58] Field of Search .............. 73/15 A, 15 B, 15 R, 73/17, 15.4; 324/140 D, 441, 443, 65 R

[56] References Cited

U.S. PATENT DOCUMENTS

| | | | |
|---|---|---|---|
| 2,769,072 | 10/1956 | Obenshain | 324/441 |
| 3,078,586 | 2/1963 | Rey | 324/61 P X |
| 3,209,249 | 9/1965 | Warfield | 73/15 R |
| 3,572,084 | 1/1969 | May | 73/15 B |
| 3,875,788 | 4/1975 | Mills | 73/15 B |
| 3,888,107 | 6/1975 | Langer et al. | 73/15 B |
| 4,154,085 | 5/1979 | Hentze | 73/15 B |

*Primary Examiner*—James J. Gill
*Attorney, Agent, or Firm*—Benasutti Associates, Ltd.

[57] ABSTRACT

A method and apparatus for determining the low temperature characteristics of materials measures the resistivity of a sample material and the resistivity of a comparision material and plots the ratio of the resistivity of the comparision material to the resistivity of the sample material versus the temperature of the sample material. In addition, the method and apparatus measures the temperature of the sample and the temperature of a reference material and plots the difference there between as a function of the temperature of the reference material. The method and apparatus is usable in monitoring and/or controlling lyophilization appartus in order to increase the efficiency of the freeze drying process, that is, increasing product yield while reducing processing time.

23 Claims, 7 Drawing Figures

METHOD AND APPARATUS FOR DETERMINING THE LOW TEMPERATURE CHARACTERISTICS OF MATERIALS

BACKGROUND OF THE INVENTION

This invention relates to the low temperature treatment of water containing solid substances for the purpose of preserving them against deterioration and more particularly to a method and apparatus determining the low temperature characteristics of such substance.

The deterioration of a wide range of solid substances, both organic and inorganic, such as food products, biological materials to be stored for medical and/or scientific purposes, e.g. fragments of animal organs and tissue; as well as various extract substances, such as serums, hormones, vitamins, and the like, such substances being included in a wide range of solid substances, both organic and inorganic, is primarily ascribable to the presence of free water and of water bonded by way of labile bonds in the molecular structure. As a result, considerable effort has been expended in an attempt to extract such water by a process that would not in turn be the cause of some irreversible effect conducive to deterioration of the treated substance.

Attempts involving direct desiccation of the substances have failed since the direct conversion of liquid water into water vapor, as by evaporation at ordinary ambient temperature in a vacuum, results in deleterious, irreversible modifications in the texture of the process materials, regardless of the precautions taken. As a result, attempts such as these have been abandoned and other methods have been investigated.

One such method, which has yielded generally satisfactory results, involves subjecting the sample to a freezing treatment in order to freeze the water as ice in situ and thereby impart a high rigidity to the physicochemical structure of the material. However, in order to preserve the frozen sample, it must be continually exposed to very low temperatures, thereby detracting from the practical value of such methods, especially in those cases where the frozen products have to be transported over long distances, or where they must be stored in quantity for long periods of time.

Another method, variously known as freeze-drying, cryo-desiccation, or lyophilization, has been developed and has yielded excellent results. This method essentially comprises a low temperature dehydration of the frozen samples by direct sublimation, under reduced pressure, of the ice in the sample. This process involves the direct conversion of the water from the solid to the vapor phase, there being an absence of liquid water. After the dehydrating step, the substance may be conveniently stored in a dry atmosphere at ordinary ambient temperatures. In order to restore the substance to its pristine form, it is only necessary to reintroduce the same amount of water into the substance as was removed during the process.

In conventional lyophilization apparatus, the ice sublimating step is generally performed in an enclosure in which a vacuum can be maintained and in which the extracted vapor is condensed on a cold surface. Since the sublimation of ice is highly endothermic (absorbing 650 calories per gram at $-30°$ C.), the temperature of the material tends to drop during the process, thereby reducing the rate at which sublimation proceeds. Consequently, in order to avoid excessive operating times, heating means must be provided which will supply heat to the material in amounts substantially equivalent to that removed by sublimation.

In prior art lyophilizing apparatus, the operation of the apparatus had been monitoring and/or controlled in terms of temperature measurement. In some apparatus, means are provided for obtaining some prescribed law of temperature variation of the product vs. time throughout the process. The methods of regulating such processes on the basis of temperature measurements suffer from an inherent disadvantage in that they do not provide any means of appreciating the actual structural modifications occuring within the processed substance during treatment at low temperatures. All that is provided is an overall indication of temperature which does not make it possible to discriminate between temperature in the dehydrated portion and temperature in the frozen portion within a given sample. In addition, temperature is not a reliable reference whereby to determine the structure of the material due to various and complex physico-chemical phenomenon such as supercooling and the like, which considerably modifies the matrix structure.

In view of the above, it has in the past been necessary to perform a number of preliminary tests which serve to evaluate the particular values to be used for the operating factors of the regulating system for each particular group of samples to be treated. In addition, a large safety margin had to be allowed for in the selection of such values if a partial or complete deterioration of materials was to be avoided. Since the actual treating temperature was thus considerably lower than the optimum temperature, the sublimation rate and hence the output rate of the process were correspondingly reduced substantially. If, on the other hand, in an attempt to increase the production rate, the operating temperature was maintained close to or equal to its highest permissible value, the product yield, meeting specifications, could be greatly reduced.

Another method of regulation or monitoring, based on a measurement of the vapor pressure present within the frozen portions and the fluid portions of the material, has been used to avoid the above stated difficulties. This method however requires the use of complex apparatus having considerable response delay or inertia. In addition, the apparatus is inherently incapable of leading to fully successful results since the only portion of the sample accessible to the measurements required is that area lying close to the interface between the dry and the frozen portions of the substance, which interface gradually advances deeper and deeper into the sample as the treatment progresses. The degree of reliable protection afforded by such monitoring methods, is therefore necessarily limited.

It has also been proposed to determine and regulate the quantity of cold units or "frigories" (negative calories) remaining available in a refrigerator, using a eutectic solution as a refrigerating medium therein, by means including a pair of electrodes contacting the eutectic solution and connected in a circuit with indicating or regulating output means, and with a DC or preferrably AC energy supply. In such systems, the measuring and/or regulating operation is based on the fact that the eutectic solution, on passing from the solid to the liquid state or vice versa, sustains a substantial change in electrical resistivity and such resistivity change is used to generate an electrical signal controlling the indicator or regulator means.

A method of controlling or monitoring the freezing and/or freeze drying operation on water containing solid substances, relating to the use of the electrical resistivity parameter, is disclosed in U. S. Pat. No. 3,078,586, issued to L. P. Rey on Feb. 26, 1963. The method of Rey consists of continually surveying, throughout the operation, the variations of a selected electric characteristic, e.g. resistivity or dielectric constant, of a sample of the substance itself being processed and eventually controlling the temperature applied to the substance so as to maintain the characteristics at a desired value at all times throughout the process. One deficiency of the method of Rey occurs when the substance is at or near the freezing point. Under these conditions, resistivity alone is not a sufficiently precise indicator to permit the process to be carried out with maximum efficiency, i.e. permitting the highest product yield in the shortest amount of time. Furthermore, resistivity alone does not provide sufficient information regarding endothermic or exothermic reactions that may result from changes in phase or structure at the freezing point of the substance.

At present, the thermal and electrical properties as a function of temperature are normally examined in separate apparatuses, and, in some cases, using different fill volumes and containers. Also, the standard differential thermal analysis equipment is not designed to accomodate a glass container that may have a volume of 100 ml. In addition, as indicated above, the variation of the magnitude of resistivity or resistance as a function of temperature is not a sharp enough indicator to distinguish the presence of mobile water. In addition, in the case of low fill volumes, the resistance of the measuring cell may be outside the upper resistance range of the instrument.

SUMMARY OF THE INVENTION

A thermal or differential thermal analysis will provide information regarding endothermic or exothermic reactions that may stem from changes in phase or structure. The resistivity method examines the electrical properties, the interface between the ice layers or between ice and interstitial layers. The use of these analytical techniques will provide information concerning the conductivity of the starting material, the degree of supercooling, presence of any metastable states of water and the temperature of any eutectic or melting point.

The results of the thermal and resistance analysis are dependent on the nature of the cooling mode, e.g., if the cooling is done by placement of the product and its container on a cold shelf or in a cold liquid. The nature of the freezing process is also dependent on the composition and dimensions of the container, volume of the product in the container and the thermal conductivity of frozen and unfrozen matrix. As a result, the thermal properties of the product should be examined in the same container and at the same full volume as that employed in the lyophilization process.

The present invention provides a method and apparatus by which thermal or differential thermal analysis and resistivity analysis may be conducted simultaneously on a material at low temperatures. The method includes the use of the ratio of the resistivity of ice to the resistivity of an ice—product matrix ($D_2$) at a given temperature in order to reveal unique low temperature characteristics of each material. The method also employs the difference between the resistance of the ice-product matrix and the resistance of an ice matrix in order to determine the low temperature properties of any specific material.

The apparatus for the present invention measures and displays the ratio of the resistivity of ice with respect to the resistivity of the ice-product matrix ($D_2$) as a function of the temperature of the product-ice matrix. The apparatus of the present invention also will measure and display the temperature differential between the temperature of the ice-product matrix and the temperature of a reference material as a function of the temperature of the reference material. In addition, the apparatus of the present invention will measure and display the temperature differential between the temperature of the ice-product matrix and the temperature of ice as a function of the temperature of the ice-product matrix.

Accordingly, it is an object of the present invention to provide a method and apparatus for accurately determining the maximum temperature at which an ice-product matrix remains completely frozen.

Another object of the present invention is the provision of a method and apparatus for maximumizing the efficiency of the freeze-drying process, that is, increasing the product yield while decreasing the time required to complete the process.

A further object of the present invention is the provision of a method and apparatus for simultaneously measuring the ratio of the resistivity of ice with respect to the resistivity of the ice-product matrix ($D_2$) and the difference between the temperature of the product and the temperature of the reference material as a function of temperature.

These and other objects of the present invention will become apparent from the following more detailed description.

DETAILED DESCRIPTION

Figure 1:
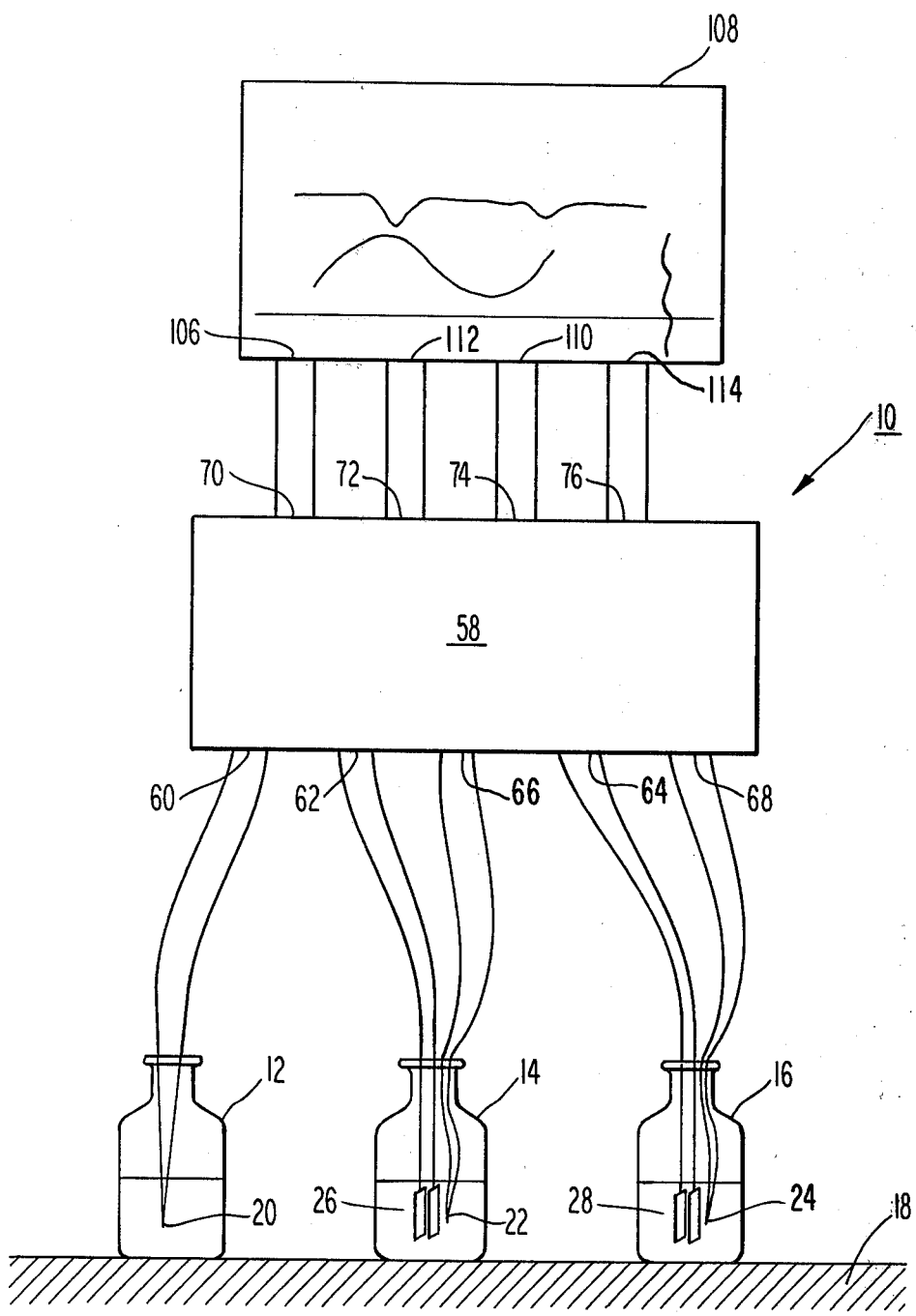
FIG. 1 is a pictorial block diagram of a preferred embodiment of the present invention.

Referring now to FIG. 1, there is shown a preferred embodiment of the apparatus of the present invention, generally designated 10. The apparatus 10 comprises first, second, and third containers; 12, 14, and 16 respectively. The containers are preferably placed on a cold shelf 18.

A temperature sensor is placed in each of the three containers. In the preferred embodiment of the apparatus 10, the temperature sensors are first, second, and third copper-constantan thermocouples, 20, 22, and 24 respectively, which thermocouples are inserted into the first 12, second 14, and third 16 containers respectively. A first pair of vertical resistivity cell electrodes, 26 are placed in the second container 14. A second pair of vertical resistivity cell electrodes 28 are placed in the third container 16.

Figure 3:
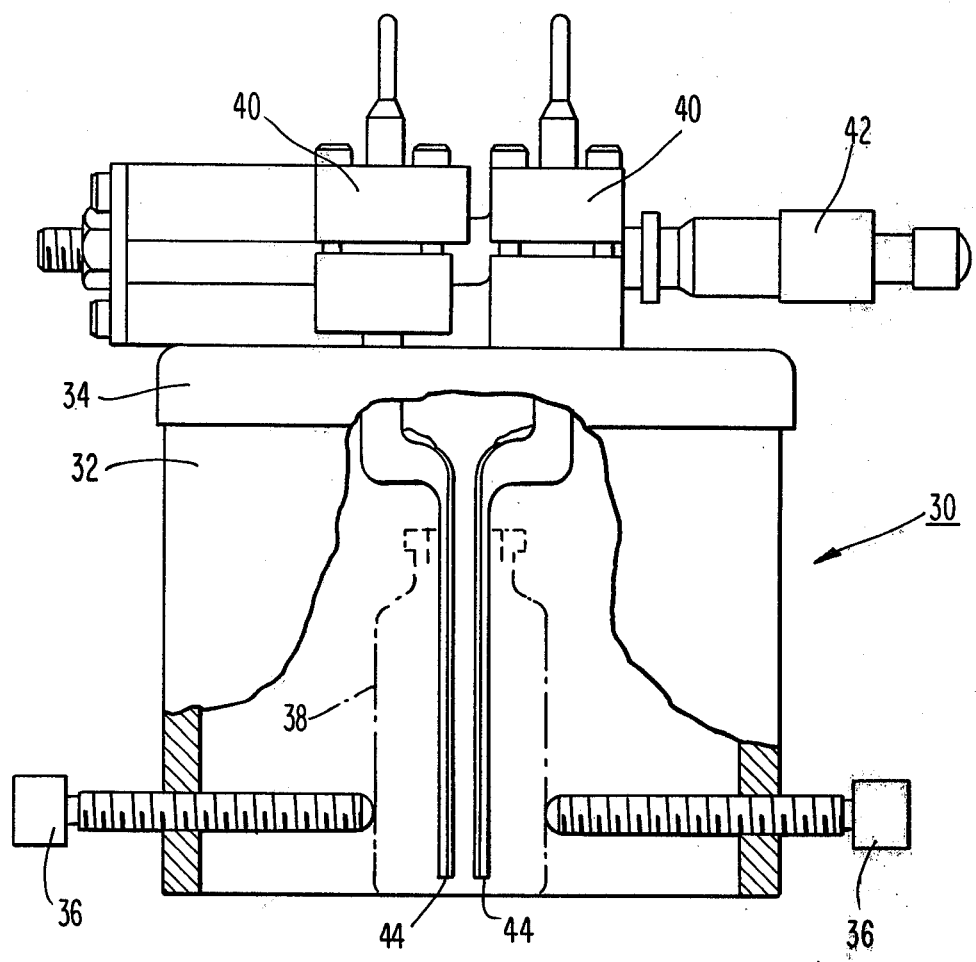
FIG. 3 is a side view, partially broken away, of a preferred embodiment of a resistivity cell for use with the apparatus of the present invention.

Referring now to FIG. 3, there is shown a preferred embodiment of a resistivity cell, generally designated 30. The resistivity cell 30 comprises a cylindrical container 32, preferably plastic, having a frame 34 mounted on the top thereof. Set screws 36 are mounted in the bottom portion in the container 32 to maintain a specimen bottle 38 in a predetermined position within the cylindrical container 32. A pair of retaining blocks 40 are mounted on the frame 34, one being rigidly attached to the frame whereby the horizontal spaced relationship between the blocks is adjustable. A micrometer drive mechanism 42 is connected to the retaining block 40 in order to afford means for precisely adjusting the horizontal spacing between the blocks. A pair of resistivity cell electrodes 44 are mounted in and insulated from the retaining block 40, one electrode being mounted in each block.

Figure 4:
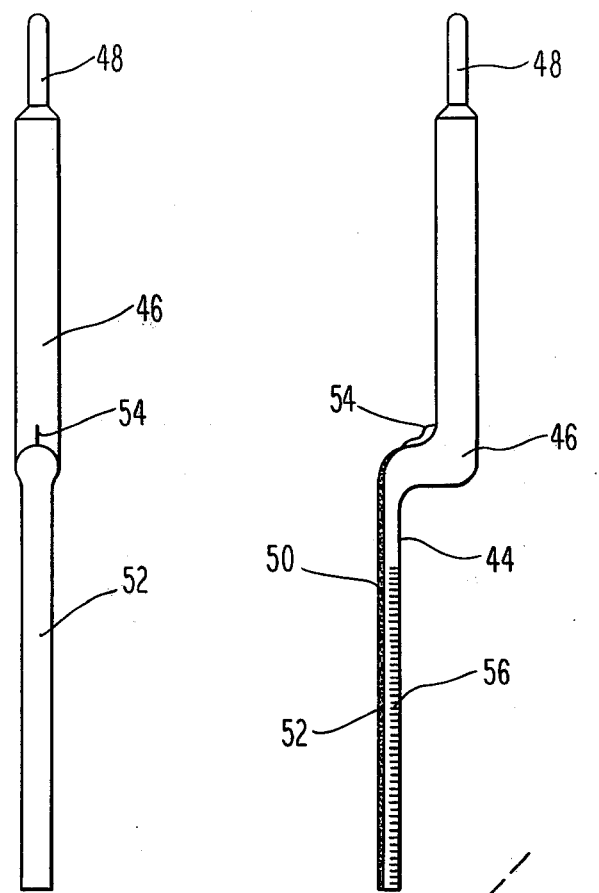
FIG. 4 depicts the preferred embodiment of one of the electrodes used in the resistivity cell shown in FIG. 3.

Referring to FIG. 4, there is shown an enlarged side view of a preferred embodiment of a resistivity cell electrode 44. The electrode 44 comprises a main frame member 46 constructed of an electrically insulated material, preferrably glass. The upper portion of the main frame member 46 has an electrode 48 mounted therein, the electrode preferably being made of copper. With the exception of a connection area at the top thereof and another smaller one at the bottom, the copper electrodes 48 is surrounded by the electrically insulated main frame member 46 in order to preclude electrical contact between the copper electrode and the retaining block 40, in which it is mounted, or between the electrode and the other portions of the resistivity cell 30. The bottom portions of the main frame member 46 has a substantially planar surface 50 on which a gold film is mounted. The gold film 52 extends over a predetermined surface area of the electrode 44 and is electrically connected to the copper electrode 48 by a platinum wire 54 in the preferred embodiment. The lower portion of the main frame 46 has a scale 56 thereon for measuring the level of material within the specimen bottle 38 after the electrodes have been inserted therein as shown in FIG. 3. It should be noted that the installed electrodes 44 are positioned such that the gold films are in a substantially parallel facing relationship with respect to each other.

Figure 2:
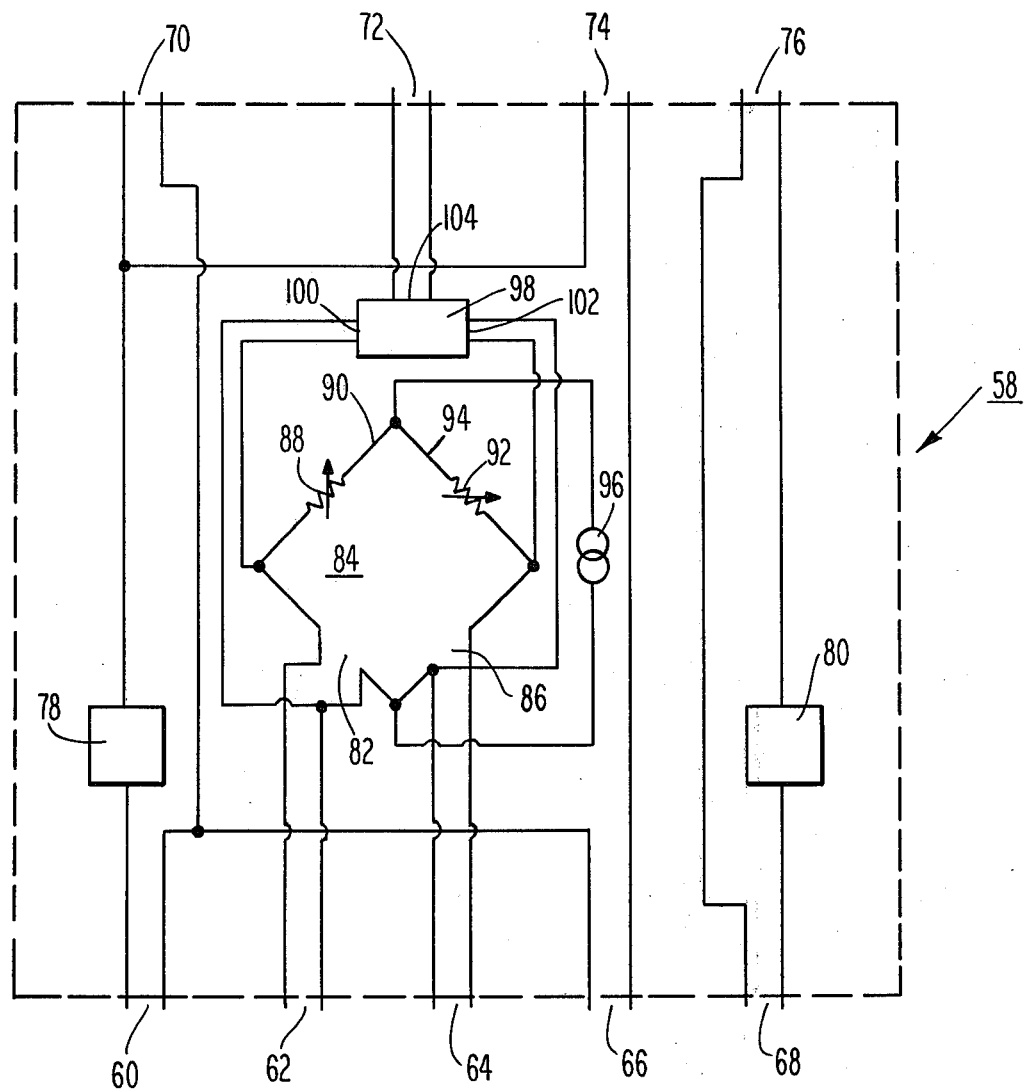
FIG. 2 is a schematic diagram of a control panel portion of FIG. 1.

Referring again to FIG. 1, the thermocouples and electrodes are electrically connected to a control panel 58. The control panel 58 includes five pairs of input terminals 60, 62, 64, 66, and 68. The control panels 58 also includes four pairs of output terminals 70, 72, 74, and 76. As shown in FIG. 2, the first pair of input terminals 60 are electrically connected to the first pair of output terminals 70 through a first 0° C. reference voltage box 78. It should be noted that an ice bath may also be used as a reference. The fifth pair of input terminals 68 are electrically connected to the fourth pair of output terminals 76 through the second 0° C. reference voltage box (or ice bath) 80. One terminal of the third pair of output terminals 74 is electrically connected to a terminal of the first 0° C. reference voltage box 78. The other terminal of the third pair of output terminals 74 is electrically connected to one terminal of the fourth pair of input terminals 66. The other terminals of fourth pair of input terminals 66 is electrically connected to one terminal of the first pair of input terminals 60 as well as one terminal of the first pair of output terminals 70.

The second pair of input terminals 62 are electrically connected across a first leg 82 of a bridge circuit 84. The third pair of input terminals 64 are electrically connected across a second leg 86 of the bridge circuit 84. Resistors 88 and 92, preferably adjustable resistors, are electrically connected across third and fourth legs, 90 and 94 respectively, of the bridge circuit 84. A power supply 96 is electrically connected between the junction of the first and second legs, 82 and 86, and the junction of the third and fourth legs, 90 and 94 of the bridge circuit 84. The power supply 96 is an AC power supply which provides power to the bridge circuit 84 at a frequency which is preferably substantially equal to 100 Hz. One input of a microcomputer 98 is electrically connected across the first leg 82 of the bridge circuit 84. A second input 102 of the microcomputer 98 is electrically connected across the second leg 86 of the bridge circuit 84. The output 104 of the microcomputer 98 is electrically connected to the second pair of output terminals 72 of the control panel 58.

As shown in FIG. 1, the first thermocouple 20 is electrically connected to the first pair of input terminals 60 of the control panel 58. The first pair of electrodes 26 are electrically connected to the second pair of input terminals 62. The second pair of electrodes 28 are electrically connected to the third pair of input terminals 64. The second thermocouple 22 is electrically connected to the fourth pair of input terminals 66. The third thermocouple 24 is electrically connected to the fifth pair of input terminals 68.

It should be noted that the first and second thermocouples 20 and 22 are connected to the first and fourth pair of input terminals 60 and 66 respectively with a polarity relationship such that the output appearing at the third pair of output terminals 74 is a function of the output (Ts), the second thermocouple 22 minus the output (Tr) of the first thermocouple 20. For example, if the positive output of the second thermocouple 22 is electrically connected to one terminal of the third pair of output terminals 74. The output from the 0° C. reference 78 is connected to the other terminal of the third pair of output terminal 74 and one terminal of the first pair of output terminals 70. The negative outputs of the first and second thermocouples 20 and 22 are electrically connected together and to the other terminal of the first pair of output terminals 70. This "bucking" arrangement of the thermocouples polarities enables a direct measurement of Ts−Tr at the third pair of output terminals 74 as well as a direct measurement of Tr at the first pair of output terminals 70.

The first pair of output terminals 70 are electrically connected to a first "x" axis input 106 of a dual channel x-y recorder 108. The third pair of output terminals 74 are electrically connected to a first "y" axis input 110 of the x-y recorder 108. The y axis 110 is related to x axis as input 106, such that the x-y recorder 108 will plot the curve which functionally relates these inputs to each other. The second pair of output terminals 72 are electrically connected to a second y axis input 112 of the dual x-y recorder 108. The fourth pair of output terminals 76 are electrically connected to a second x axis input 114 of the dual x-y recorder 108. The dual x-y recorder will plot the functional relationship between the signal present at the second y axis input and the signal present at the second x axis input. Note that while the preceeding described the use of a dual channel x-y recorder to plot the functional relationships, the x-y recorder can be replaced by a cathode ray tube (CRT)

display and/or printer by incorporating appropriate conversion and formating equipment as will be subsequently described.

The method of obtaining the low temperature characteristics of a material in accordance with the present invention, using the apparatus previously described, is as follows. Based on the height of the liquid in the second and third containers, 14 and 16, the space in between the electrodes 44 in each of those containers is adjusted such that the cell constants are substantially equal and the resistance of the cells will approximate the values of first and second resistors, 88 and 92, of the bridge circuit 84. Since the cell constant of a resistivity cell is defined:

$$K = \frac{(w)(h)}{d}$$

where w equals the width of the electrodes 44, h equals the height of the liquid level in the specimen bottle 38, and the d equals the distance separating the electrodes adjusting the spacing between the electrodes 44, using the micrometer drive mechanism 42 will allow the establishment of a desirable cell constant K.

Distilled water is then added to the second and third containers, 14 and 16, and the bridge circuit 84 is balanced by adjusting the first and second resistors 88 and 92 as well as further adjustment of the electrodes spacing in the containers, if necessary. The bridge is properly balanced when the cell constants are equal and the output voltage appearing at the second pair of output terminals 72 is equal to a predetermined value representing unity.

The microcomputer 98 is preprogrammed to perform certain operations as will be substantially defined. The microcomputer 98, as shown in FIG. 2, is also defined to include an A to D converter at each of the inputs 100 and 102 for converting the analog voltage appearing across the first and second legs, 82 and 86, into a digital format usable by the microcomputer, as is well known in the computer art. In addition, the block also is defined to include a digital to analog converter at the output 104, of the microcomputer to convert the digital format, usable by the microcomputer 98, into an analog voltage for subsequent processing by the x-y recorder.

The voltage appearing across the first leg 82 of the bridge circuit 84 is representative of the resistivity of the material in the second container 14. Likewise, the voltage appearing across the second leg 86 of the bridge circuit 84 is representative of the resistivity of the material in the third container 16. The microcomputer 98 receives these voltages through the first 100 and second 102 inputs respectively, converts these analog voltages into usable digital formats as previously explained, then calculates a value for D2 which is defined to equal, in the preferred embodiment shown and described herein, the resistivity of material in the third container 16 divided by the resistivity of the material in the second container 14. The magnitude of the value of D2 is then converted from the digital format into an analog voltage in a range of magnitude acceptable by the x-y recorder 108. When the voltage across the first leg 82 of the bridge circuit 84 is equal to the voltage across the second leg 86, the microcomputer 98 will output an analog voltage which will, by definition, have a value which represents unity, since under these conditions D2 is equal to 1.

Figure 6:
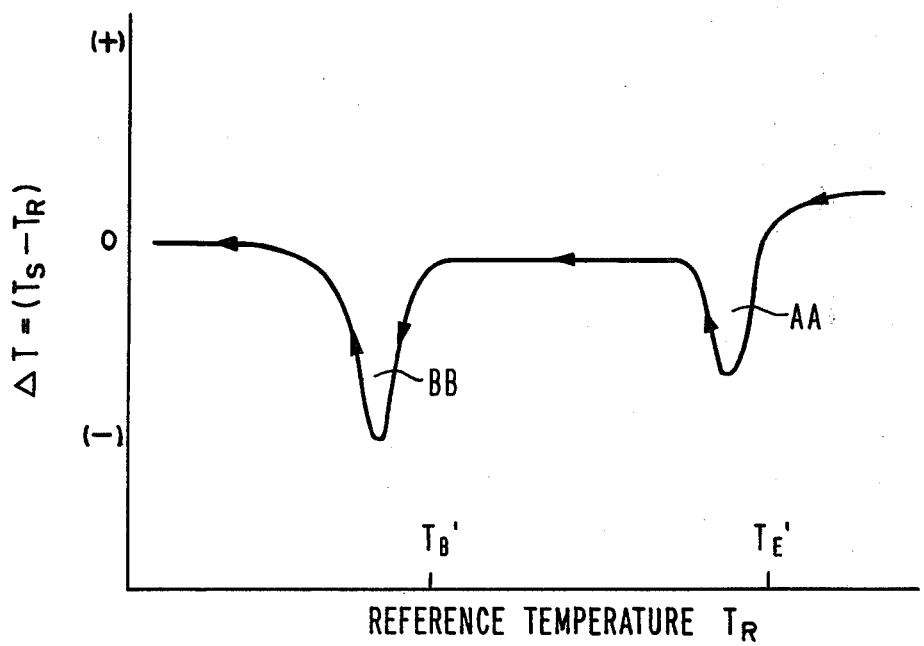
FIG. 6 is a differential thermal analysis plot.

After the bridge circuit 84 has been zeroed, that is when the cell constants are equal and the output voltage from the microcomputer 98 has a unit value, as previously described, the distilled water is removed from the second container 14 and replaced with a sample of the product. A reference material which does not undergo a phase change over the temperature range employed, such as methinol in the preferred embodiment, is added to the first container 12. The temperature of the cold shelf 18 is then cooled. A differential thermal analysis trace is displayed on the x-y recorder, since the voltage output from the first pair of output terminals 70, which, as previously stated, is representative of the temperature (Tr) of the reference material in the first container 12, is connected to the first x axis input of the recorder and the voltage output from the third pair of output terminals 74, which, as previously stated, is representative of Ts−Tr is connected to the first y axis input of the x-y recorder. Consequently, the trace displayed is indicative of the relationship between the temperature of the product and the temperature of the reference material. FIG. 6 depicts a typical thermal analysis plot. In particular, FIG. 6 shows a differential thermal analysis trace of the product during warming. Examination of this plot shows that at the outset of the warming, $\Delta T$ was greater than zero. $\Delta T$ will be greater than zero because of the difference in the thermal properties of the product (solid) and the reference (liquid). The indicated phase change at $T'_E$ is associated with the appearance of the eutectic point, while the temperature $T'_B$ indicated the melting point of the ice. The area AA can be used to estimate the heat of fusion for the eutectic and the quantity of water can only be approximated from the Area BB. A knowledge of the heat of fusion of the eutectic can provide one with an estimate as to the rate of melting, using the relationship:

$$\frac{d\lambda}{dt} = \frac{(q_s - q_l)}{D\,A\,\Delta Hf}$$

where $q_s$ is the heat transport through the ice crystal, $q_l$ is the heat transport across the liquid-solid interface, D is ice density, A is the cross sectional area of the ice crystal and $\Delta Hf$ is the heat of fusion of ice (79 cal./g).

In addition, to displaying the differential thermal analysis trace, the dual trace x-y recorder also displays D2 as a function of temperature analysis trace, since the output voltage from the microcomputer 98, which represents the magnitude of D2 is connected to the second y axis input of the x-y recorder while the second x axis input is driven either from the output of the third thermocouple 24 measuring the temperature of the distilled water in the third container 16 or from the second thermocouple 22 whose output indicates the temperatures of the product in the second container 14.

Figure 7:
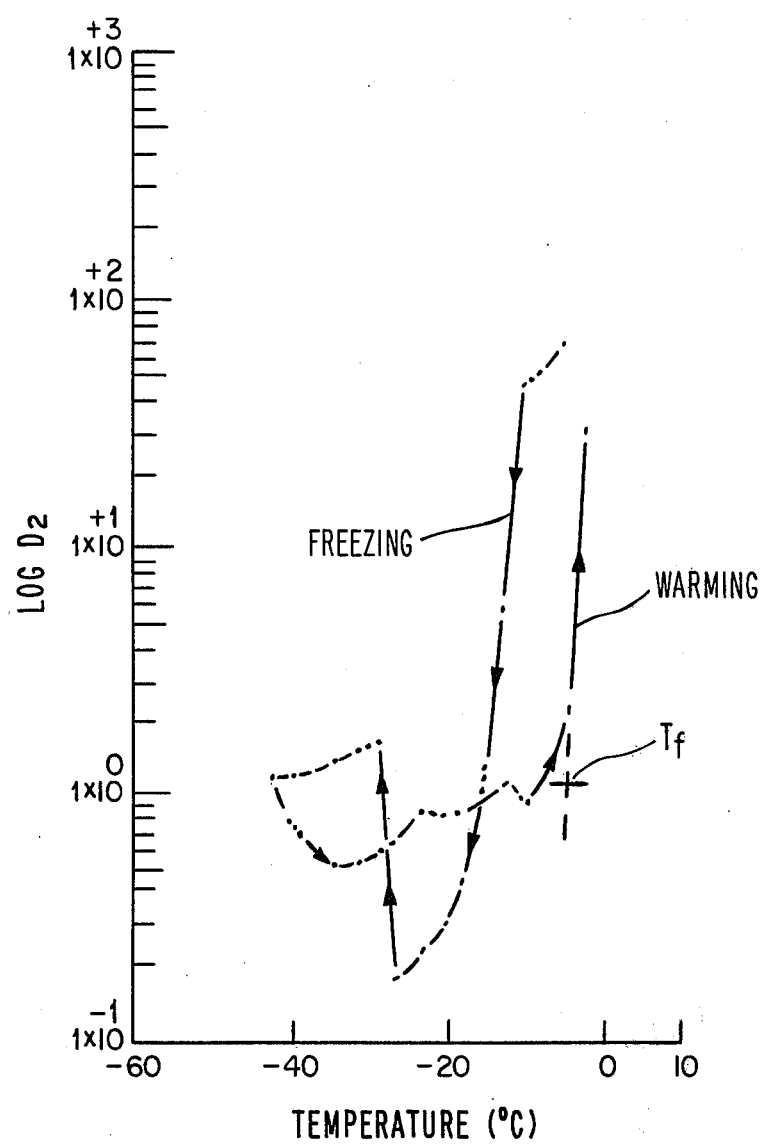
FIG. 7 is a plot of the log $D_2$ for an ice-product matrix as a function of temperature.

FIG. 7 shows a typical log D2 plot as a function of temperature. In particular, FIG. 7 depicts a a plot of the log D2 as a function of temperature for a freezing and warming cycle of an ice-mannitol matrix. This Figure shows that the freezing is complete near a temperature of −15° C. i.e., $D_2 = 1$. Further lowering of the temperature decreased the value of $D_2$ until about −30° C. there was a sharp increase in the value of $D_2$. As the ice-mannitol matrix was warmed, the value of $D_2$ remained less than 1 until a temperature of −8° C. was reached. Extrapolation of the best fit through $D_2$ values back to $D_2 = 1$ gave a temperature of $T_f = -5.5$ C. at a resistivity of $3 \times 10^8$ ohm-cm.

Because of the versatility of the microcomputer 98 which is a part of the apparatus of the present invention, the $D_2$ output can be displayed in terms of $D_2$ or log $D_2$. As shown in FIG. 7, the analysis is conducted for both the freezing and thawing of the product. It should be noted that $D_2$ could also be expressed in terms of R (b) – R (ice) where R (b) is the resistance of the second cell 14 and R (ice) is the resistance of the third cell 16. It should be also noted that expressing $D_2$ as a difference would remove the necessity for the incorporation of the microprocessor, but it would also substantially decrease the sensitivity of the measurement.

Figure 5:
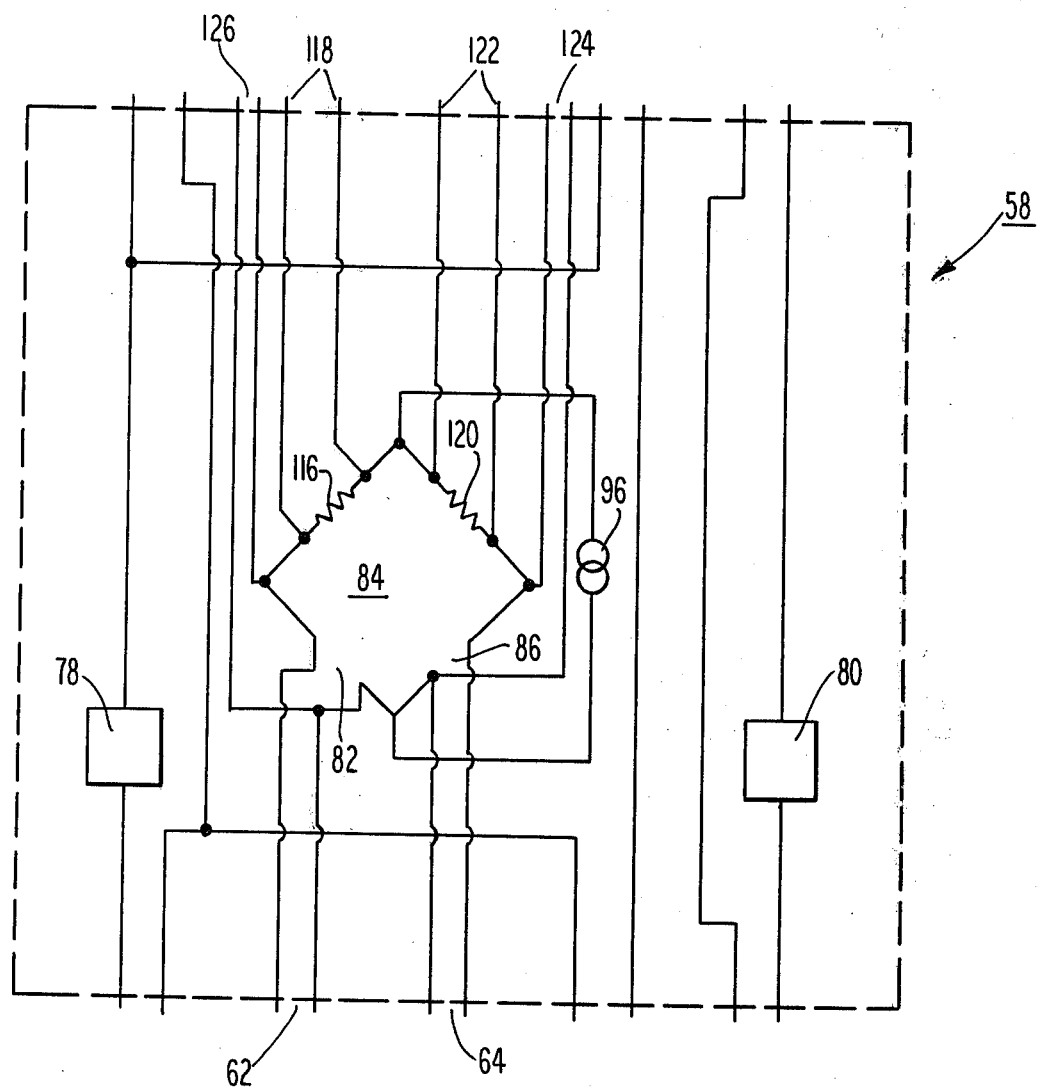
FIG. 5 is a schematic block diagram of an alternate preferred embodiment of the control panel portion of the apparatus of the present invention.

Referring to FIG. 5, there is shown an alternate embodiment of the control panel 58. The alternate embodiment depicted in FIG. 5, is similar to the previous embodiment described with reference to FIG. 2 with the following differences. The voltage across the first resistor 116 appears the output terminals 118 while the voltage across the second resistor 120 appears across the output terminals 124 since the output terminals 124 are electrically connected across the second leg 86 of the bridge circuit 84 which in turn is electrically connected to the third pair of input terminals 64 as previously described. The voltage drop across the electrodes of the second container 14, which contain the product, appears at the output terminal 126 since the output terminals 126 are electrically connected across the first leg 82 of the bridge 84 which is in turn electrically connected to the second pair of input terminal 62.

The output terminal 118, 122, 124, 126, are electrically connected to an A to D converter (not shown) for converting the analog signals appearing at these output terminals to a digital format usable by a microprocessor. The microprocessor is preprogrammed to calculate the value of $D_2$ as:

$$D_2 = \frac{V_{124} \cdot R_{120} \cdot V_{118}}{V_{122} \cdot R_{122} \cdot V_{126}}$$

where $V_{118}$, $V_{122}$, $V_{124}$, and $V_{126}$ are the voltages across the terminals 118, 122, 124, 126 respectively and $R_{116}$ and $R_{120}$ are the values of the first 116 and the second 120 resistors respectively of the bridge circuit 84.

The digital output representative of the quantity D may go either to a digital to analog converter for converting to analog form for subsequent display by an x-y recorder as previously described or the digital output may be sent directly to a terminal incorporating a cathode ray tube (CRT) display and/or a printer whereupon the curves are displayable on the screen of the CRT and/or a hard copy made by the printer when such a terminal is used, the analog output of the thermocouples which were input to the x-y recorder as previously described, would be input to an analog to digital converter and then to the terminal for display as is well known in the computer art.

Note that the method and apparatus of the present invention is useful not only in determining the low temperature characteristics of water containing substances as set forth previously, they are useful in determining the low temperature characteristics of any material which undergoes a phase change and such applications are considered by the inventor to be within the scope and principle of the present invention.

It will be understood that various changes in the details, materials, and arrangement of parts which are herein described and illustrated in order to explain the nature of this invention, may be made by those skilled in the art within the principle and scope of the invention as expressed in the following claims.

I claim:

1. A method of determining low temperature characteristics of a sample material comprising the steps of:
   (a) varying the temperature of said sample material and a comparison material;
   (b) measuring electrical resistivity of said sample material;
   (c) measuring electrical resistivity of said comparison material;
   (d) measuring the temperature of said sample material as a reference temperature; and
   (e) plotting ratio $D_2$ of the resistivity of said comparison material to the resistivity of said sample material as a function of said reference temperature.

2. The method of claim 1 wherein step (d) comprises measuring the temperature $T_S$ of said sample material.

3. The method of claim 1 wherein step (d) comprises measuring the temperature of said comparison material.

4. The method of claim 2 or claim 3 wherein step (a) further comprises the steps of cooling said sample material and said comparison material to a first pre-determined temperature below the freezing points thereof then warming said materials to a second pre-determined temperature.

5. The method of claim 4 wherein said sample material is a water containing material and step (c) comprises measuring the electrical resistivity of ice.

6. The method of claim 5 wherein step (a) comprises varying the temperature of said sample material, said comparison material and a reference material, and comprising the additional steps of:
   (f) measuring the temperature $T_R$ of said reference material; and
   (g) plotting the difference $\Delta T_{DTA}$ of $T_S$ minus $T_R$ as a function of $T_R$.

7. The method of claim 6 wherein step (f) comprises measuring the temperature $T_R$ of Methanol.

8. An apparatus for determining low temperature characteristics of a sample material comprising:
   (a) means for varying the temperature of said sample material and a comparison material;
   (b) means for measuring electrical resistivity of said sample material;
   (c) means for measuring electrical resistivity of said comparison material;
   (d) means for measuring the temperature of said sample material as a reference temperature; and
   (e) means for plotting a ratio $D_2$ of the resistivity of said comparison material to the resistivity of said sample material as a function of said reference temperature.

9. The apparatus in accordance with claim 8 wherein said means for measuring the electrical resistivity of said sample material comprises a resistivity cell having an adjustable cell constant.

10. The apparatus in accordance with claim 9 wherein said means for measuring the electrical resistivity of said comparison material comprises a resistivity cell having an adjustable cell constant.

11. The apparatus in accordance with claim 10 wherein said means for plotting the ratio $D_2$ comprises computer means for accepting the measurement of the electrical resistivity of said sample material, accepting the measurement of the electrical resistivity of said comparison material, providing an output which is a function of the value of the ratio of the latter measurement to the former measurement, and data display means for accepting the output of said computer means and the measurement of said reference temperature and providing a visual display of the functional relationship there between.

12. The apparatus in accordance with claim 11 wherein said data display means comprises an X-Y recorder.

13. The invention of claim 11 wherein said data display means comprises a Cathode Ray Tube Terminal.

14. The apparatus in accordance with claim 11 wherein said data display means comprises a digital printer.

15. An apparatus for determining low temperature characteristics of a sample material comprising:
(a) means for varying the temperature of said sample material, a comparison material, and a reference material;
(b) means for measuring electrical resistivity of said sample material;
(c) means for measuring electrical resistivity of said comparison material;
(d) means for measuring the temperature of said sample material as a reference temperature;
(e) means for plotting a ratio $D_2$ of the resistivity of said comparison material to the resistivity of said sample material as a function of said reference temperature;
(f) means for measuring the temperature $T_s$ of said sample material;
(g) means for measuring the temperature $T_R$ of said reference material; and
(h) means for plotting the difference $\Delta T_{DTA}$ of $T_S$ minus $T_R$ as a function of $T_R$.

16. An apparatus in accordance with claim 15 wherein said means for measuring the electrical resistivity of said sample material comprises a resistivity cell having an adjustable cell constant.

17. The apparatus in accordance with claim 16 wherein said means for measuring the electrical resistivity of said comparison material comprises a resistivity cell having an adjustable cell constant.

18. The apparatus in accordance with claim 17 wherein said means for plotting the ratio $D_2$ comprises computer means for accepting the measurement of the electrical resistivity of said sample material, accepting the measurement of the electrical resistivty of said comparison material, providing an output which is a function of the value of the ratio of the latter measurement to the former measurement, and data display means for accepting the output of said computer means and the measurement of said reference temperature and providing a visual display of the functional relationship there between.

19. The apparatus in accordance with claim 18 wherein said means for plotting the difference $\Delta T_{DTA}$ of $T_S$ minus $T_R$ as a function of $T_R$ comprises data display means for accepting a signal which is a function of the value of the quantity $T_S$ minus $T_R$ as well as the measurement of said reference temperature $T_R$ and providing a visual display of the functional relationship there between.

20. The apparatus in accordance with claim 19 wherein said data display means comprises a dual channel X-Y recorder.

21. The invention of claim 20 wherein said data display means comprises a Cathode Ray Tube Terminal.

22. The apparatus in accordance with claim 21 wherein said data display means comprises a digital printer.

23. An apparatus for controlling or monitoring a freeze drying operation on water—containing solid substance for the preservation of said substances, said apparatus comprising:
(a) means for varying the temperature of said water—containing solid substance, ice, and a reference material;
(b) means for measuring electrical resistivity of said water—containing solid substance;
(c) means for measuring electrical resistivity of said ice;
(d) means for measuring the temperature $T_S$ of said water—containing solid substance;
(e) means for providing a first signal, the magnitude of which is a function of the magnitude of the ratio $D_2$ of the resistivity of said ice to the resistivity of said water—containing solid substance;
(f) means for providing a controlled signal when the magnitude of said first signal has reached a predetermined value;
(g) means for plotting $D_2$ as a function of said temperature $T_S$; and
(h) means for measuring the temperature $T_R$ of said reference material; and means for plotting the difference $\Delta T_{DTA}$ of $T_S$ minus $T_R$ as a function of $T_R$.

* * * * *